United States Patent [19]

König et al.

[11] 4,039,673
[45] Aug. 2, 1977

[54] PENICILLINS AND CEPHALOSPORINS AND THEIR PRODUCTION

[75] Inventors: Hans-Bodo König; Karl Georg Metzger; Wilfried Schröck, all of Wuppertal, Germany

[73] Assignee: Bayer Aktiengesellschaft, Germany

[21] Appl. No.: 643,550

[22] Filed: Dec. 22, 1975

Related U.S. Application Data

[62] Division of Ser. No. 518,178, Oct. 25, 1974, Pat. No. 3,966,709.

[30] Foreign Application Priority Data

Oct. 30, 1973    Germany ............................ 2354219

[51] Int. Cl.² ........................................... A61K 31/43
[52] U.S. Cl. ................................... 424/271; 424/246; 260/239.1; 544/28
[58] Field of Search ......................................... 424/271

[56] References Cited

FOREIGN PATENT DOCUMENTS 767,647   11/1971   Belgium
767,648   11/1971   Belgium

*Primary Examiner*—Jerome D. Goldberg
*Attorney, Agent, or Firm*—Jacobs & Jacobs

[57] ABSTRACT

β-Lactams of the formula

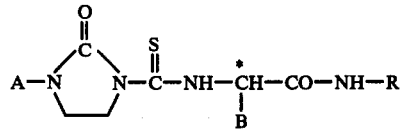

and pharmaceutically acceptable nontoxic salts thereof wherein
A is hydrogen or alkyl of 1 to 4 carbon atoms;
B is phenyl, methylphenyl, chlorophenyl, hydroxyphenyl or cyclohexa-1,4-dien-1-yl;
R is a moiety of the formula

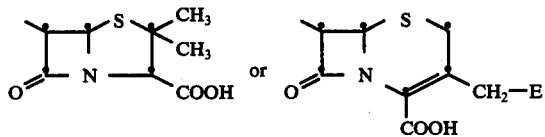

wherein
E is hydrogen, —OH or —O—CO—CH₃; and
C* constitutes a center of chirality;
are produced which exhibit antibiotic activity.

12 Claims, No Drawings

PENICILLINS AND CEPHALOSPORINS AND THEIR PRODUCTION

CROSS-REFERENCE

This is a division of Ser. No. 518,178 filed Oct. 25, 1974, now U.S. Pat. No. 3,966,709 issued June 29, 1976.

The present invention is concerned with new β-lactam compounds, a process for their production, pharmaceutical compositions wherein said β-lactams are the active ingredient, and to methods of treating bacterial infections in humans and animals which comprises administering said compounds to such humans or animals. In addition, the present invention includes growth-promoting compositions wherein said β-lactams are the active ingredients and animal fodders, including methods of improving fodder utilization in animals utilizing said β-lactams.

It is known in the art that certain α-(imidazolidin-2-oxo-1-yl-carbonylamino)-benzylpenicillins exhibit antibacterial activity. (See Belgian Pat. Nos. 767,647 and 767,648, Dutch Pat. No 7,114,254 and German Offenlegungsschrift No. 2,152,968.)

The β-lactams according to the present invention differ chemically from these known compounds and in particular, they differ in that the imidazolidinone moiety is linked to the 6- or 7-position side-chain not via a carbonyl group, but via a thiocarbonyl group. Moreover, there is no acyl moiety on the nitrogen atom at the 3-position of the imidazolidinone group.

More particularly, the present invention is concerned with penicillins and cephalosporins of the formula

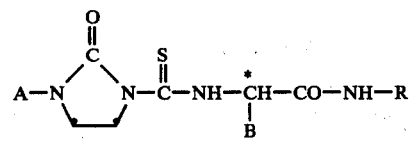

(I)

or a pharmaceutically acceptable nontoxic salt thereof
wherein
A is hydrogen or alkyl of 1 to 4 carbon atoms;
B is phenyl, methylphenyl, chlorophenyl, hydroxyphenyl or cyclohexa-1,4-dien-1-yl;
R is a moiety of the formula

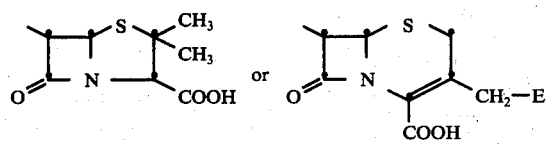

wherein
E is hydrogen, —OH or —O—CO—CH$_3$; and
C* constitutes a center of chirality.

These penicillins and cephalosporins are particularly useful for their antibacterial activity and, most surprisingly, they were found to exhibit a substantially greater level of antibacterial activity, especially against bacteria from the family of the Enterobacteriaceae, than the penicillins and cephalosporins known in the art.

The compounds of the present invention are produced by reacting a compound of the formula

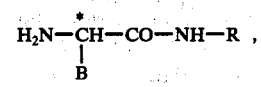

(II)

wherein
R is as above defined,
with a compound of the formula

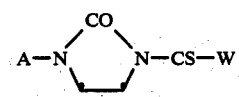

(III)

wherein
A, B and C* are as above defined, and W is halogen or azido,
in the presence of a diluent and an acid-binding agent at a temperature of from −20° to +50° C, and, in the case of the salts, reacting the free acid with a suitable base, and recovering the compound produced.

If, for example, D α-aminobenzylpenicillin and 1-chlorothiocarbonyl-imidazolidin-2-one are used as starting compounds, the course of the reaction can be represented by the following equation:

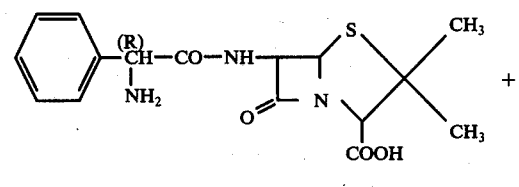

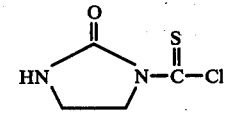

(Tetrahydrofuran H$_2$O)

(0°–20° C, pH=6.5–7.5)

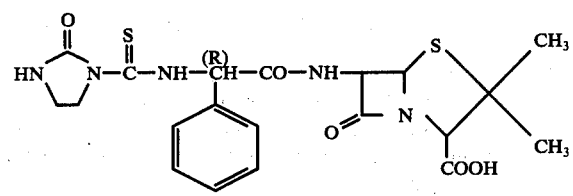

According to one embodiment of the present invention, R is

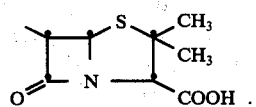

According to another embodiment of the present invention, R is

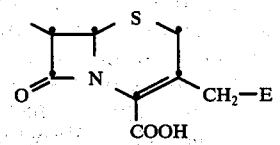

According to another embodiment of the present invention, B is phenyl, paramethylphenyl, parachlorophenyl, parahydroxyphenyl, or cyclohexa-1,4-dien-1-yl.

According to another embodiment of the present invention
A is hydrogen, methyl or ethyl; and
B is phenyl, paramethylphenyl, parachlorophenyl, parahydroxyphenyl, or cyclohexa-1,4-dien-1-yl.

According to another embodiment of the present invention
A is hydrogen, or methyl; and
B is phenyl, paramethylphenyl, parachlorophenyl, parahydroxyphenyl, or cyclohexa-1,4-dien-1-yl.

According to another embodiment of the present invention
A is hydrogen;
B is phenyl, p-hydroxyphenyl or cyclohexa-1,4-dien-1-yl; and
R is

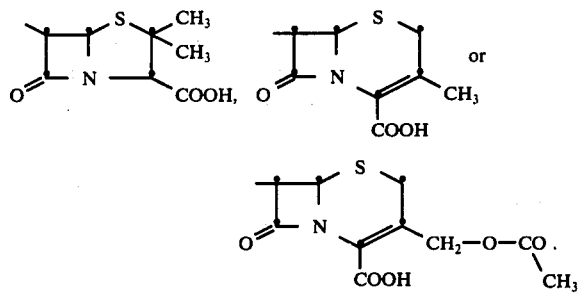

According to another embodiment of the present invention
A is hydrogen or methyl;
B is phenyl, p-hydroxyphenyl or cyclohexa-1,4-dien-1-yl; and
E is —O—CO—CH₃.

According to another embodiment of the present invention
A is hydrogen;
B is phenyl, p-hydroxyphenyl or cyclo-hexa-1,4-dien-1-yl; and
E is hydrogen or —O—CO—CH₃.

W is preferably fluorine, chlorine or bromine, particularly chlorine or bromine, especially chlorine.

The penicillins and cephalosporins of the present invention form salts with all of the bases normally employed in pharmaceutical chemistry and, particularly, as is known in the penicillin and cephalosporin art. Representative bases include alkali metal hydroxides and alkaline earth metal hydroxides, alkali metal carbonates and alkaline earth metal carbonates and alkali metal bicarbonates (such as sodium hydroxide and potassium hydroxide, calcium hydroxide and magnesium hydroxide, sodium carbonate and potassium carbonate, calcium carbonate, sodium bicarbonate and potassium bicarbonate), and also aluminum and ammonium hydroxides. Organic amines can also be used, including primary, secondary and tertiary aliphatic amines, as well as heterocyclic amines. Representative organic amines include di-(lower alkyl)-amines and tri-(lower alkyl)-amines (for example, diethylamine and triethylamine), tri-β-hydroxyethylamine, procaine, dibenzylamine, N,N'-dibenzylethylenediamine, N-benzyl-β-phenylethylamine, N-methylmorpholine and N-ethylmorpholine, 1-ephenamine, dehydroabietylamine, N,N'-bis-dehydroabietylethylenediamine and N-lower alkylpiperidine.

The center of chirality C* can be in either the D = R or the L = S form, but the former is preferred. Other centers of assymmetry may, of course, also be present in the molecule and give rise to optical isomerism.

The β-lactams of the present invention may be present in the form of hydrates and different crystalline forms. The hydrates and various crystalline forms are generally equivalent in antimicrobial action to each other and to the anhydrous form.

The present invention includes the optical isomers, epimers and racemates, as well as the crystalline forms and hydrates.

The starting materials of formula II above are generally known in the art. Representative compounds include:
α-aminobenzyl-penicillin,
α-amino-p.-hydroxybenzylpenicillin,
α-amino-p.-methylbenzylpenicillin,
α-amino-p.-chlorobenzylpenicillin,
6-[2-amino-2-(cyclohexa-1,4-dien-1-yl)-acetamido]-penicillanic acid,
7-(α-amino-phenylacetamido)-3-methyl-ceph-3-em-4-carboxylic acid and
7-(α-amino-phenylacetamido)-3-acetoxymethyl-ceph-3-em-4-carboxylic acid.

The compounds of formula III used as starting materials are either known or are obtainable according to techniques and procedures per se known. They can be prepared, for example, from compounds of the formula

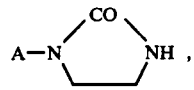

(IV)

wherein A is as above defined, and thiophosgene.

Those compounds of formula III wherein W is azido can be obtained in the customary manner; for example, from the corresponding compounds III wherein W is halogen, for example, by reaction with alkali metal azides.

Representative starting compounds of the formula III include:
1-chlorothiocarbonyl-2-oxo-imidazolidine,
1-chlorothiocarbonyl-2-oxo-3-methyl-imidazolidine,
1-chlorothiocarbonyl-2-oxo-3-ethyl-imidazolidine,
1-azidothiocarbonyl-2-oxo-imidazolidine,
1-azidothiocarbonyl-2-oxo-3-methyl-imidazolidine and
1-azidothiocarbonyl-2-oxo-3-ethyl-imidazolidine.

Diluents which can be used in the process according to the invention include water and all inert organic solvents, preferably those which are water-miscible. These include di-(lower alkyl)-ketones (for example acetone and methyl ethyl ketone), cyclic ethers (for example tetrahydrofuran and dioxane), nitriles (for example acetonitrile), di-(lower alkyl)-formamides (for example dimethylformamide), alkyl alcohols (for example ethanol and isopropanol), and dimethylsulphoxide. These diluents can also be used as mixtures with one another and as any desired mixtures of one or more of these solvents with water. Thus, the process according to the invention can be carried out in the presence of: (a) only water; (b) only one or more organic diluents or (c)

water and one or more organic diluents. If pH measurement during the reaction according to the invention is feasible, because of the presence of water, the pH of the reaction mixture is preferably kept between 6.5 and 7.5 by adding bases or by using buffer mixtures. However, the reaction according to the invention can also be carried out in a different pH range, for example between 4.5 and 9.0, or at pH 2.0 to 4.5. Further, it is possible to carry out the reaction with water-immiscible diluents, for example halogenated hydrocarbons (such as chloroform or methylene chloride), with addition of, preferably, (lower alkyl) amines, such as triethylamine or diethylamine, or with addition of N-ethylpiperidine. The reaction can also be carried out in a mixture of water and a water-immiscible diluent, for example, a lower alkyl ether (such as diethyl ether), a halogenated hydrocarbon (such as chloroform or methylene chloride), carbon disulphide, isobutyl methyl ketone, an ester (such as ethyl acetate), or an aromatic hydrocarbon (such as benzene); it is desirable to stir the mixture vigorously and to keep the pH value between 4.5 and 9.0 or, for example, between 2.0 and 4.5, by addition of bases or by the use of conventional buffer solutions. However, the reaction can also be carried out in water alone, in the absence of organic solvents, in the presence of an organic or inorganic base or with addition of customary buffer substances.

As acid-binding agents, any of the normally used acid-binding agents which one of ordinary skill in the art of β-lactam antibiotics would use are applicable. These include inorganic bases, and organic bases which are difficult to acylate, for example due to steric hindrance. Sodium hydroxide and potassium hydroxide may be mentioned as examples of inorganic bases. As examples of organic bases there may be mentioned tertiary amines, for example triethylamine and pyridine, and, as a secondary amine which is difficult to acylate, dicyclohexylamine.

While the reaction temperature is generally from about −20° to about +50° C, a preferred temperature range is from 0° to +20° C.

As is the case with most chemical reactions, higher or lower temperatures than those indicated can be used. However, if the values mentioned in the examples are substantially exceeded, side reactions will increasingly occur which will have the effect of reducing the yield and/or affecting the purity of the final products. On the other hand, excessively lowered reaction temperatures reduce the speed of the reaction, often so greatly that the yields may be substantially decreased.

The reaction of the present invention can be carried out under normal pressure or under reduced or elevated pressure. Generally, it is carried out under atmospheric pressure.

In carrying out the process of the present invention, the reactants of the formulae II and III can be reacted with one another in equimolar amounts. However, it can be desirable to use one of the two reactants in excess so as to facilitate the purification of the desired penicillin, or its preparation in a pure form, and to increase the yield.

For example, the reactants of the formula II can be employed in an excess of 0.1 to 0.3 mol equivalent and decreased decomposition of the reactants of the formula III in an aqueous solvent mixture can thereby be achieved. The excess of the reactants of the formula II can be removed readily during working up of the reaction mixture, because of the good solubility of these reactants in aqueous mineral acids.

On the other hand, it is also possible, with advantage, to employ the reactants of the formula III in an excess of, for example, 0.1 to 1.0 mol equivalent. This results in better utilization of the reactants of the formula II and compensates the decomposition of the reactants of the formula III which takes place as a side reaction in aqueous solvents. Since the compounds of the formula III added in excess rapidly becomes converted, in water, into neutral nitrogen-containing heterocyclic compounds which can easily be removed, the purity of the antibiotics is hardly impaired thereby.

The amount of the base used is determined, inter alia, by what particular pH it is desired to maintain. Where pH measurement and adjustment is not carried out or is not possible or not meaningful because of the absence of sufficient amounts of water in the diluent, 2 mol equivalents of base are preferably added.

The working up of the reaction batches in order to prepare the compounds of the present invention can be carried out throughout in the manner generally known for these substances. The isolation and purification of the compounds of the present invention can also be carried out in accordance with generally customary methods of organic chemistry.

The following β-lactams are representative of those of the present invention:

D—α-[(2-oxo-imidazolidin-1-yl)-thiocarbonylamino]-benzylpenicillin,

D—α-[(2-oxo-imidazolidin-1-yl)-thiocarbonylamino]-p.-hydroxy-benzylpenicillin,

D—α-[(2-oxo-imidazolidin-1-yl)-thiocarbonylamino]-2,5-dihydro-benzylpencillin,

7-{D—α-[(2-oxo-3-methyl-imidazolidin-1-yl)-thiocarbonylamino]-phenylacetamido}-3-acetoxymethyl-ceph-3-em-4-carboxylic acid, 7-{D—α-[(2-oxo-imidazolidin-1-yl)-thiocarbonylamino]-phenylacetamido}-3-acetoxymethyl-ceph-3-em-4-carboxylic acid, D—α-[(3-methyl-2-oxo-imidazolidin-1-yl)-thiocarbonylamino]-benzylpenicillin, and D—α-[(3-methyl-2-oxo-imidazolidin-1-yl)-thiocarbonylamino]-p.-hydroxy-benzylpencillin.

The β-lactams of the present invention exhibit a broad spectrum of antimicrobial activity. They can be used to combat a broad range of both Gram-positive and Gram-negative bacterial infections and can also be used for preserving inorganic and organic materials such as polymers, lubricants, paints, fibers, leather, paper timber, foodstuffs, water and the like.

Because of their antibacterial activity, they are particulary useful for the prophylaxis and treatment of topical and systemic infections; for example, those caused by:

Micrococcaceae, such as Staphylococci (for example *Staphylococcus sureus, Staph. epidermidis, Staph. aerogenes* and *Gaffkya tetragena* (Staph. = Staphylococcus));

Lactobacteriaceae, such as Streptococci (for example *Streptococcus pyogenes*, α- and β-haemolytic Streptococci, non-(Y)-haemolytic Streptococci, *Str. viridans. Str. faecalis* (Enterococci), *Str. agalactiae, Str. lactis, Str. equi. Str. anaerobis* and Diplococcus pneumoniae (Pneumococci) (Str. = Streptococcus);

Neisseriaceae, such as Neisseriae (for example *Neisseria gonorrhoeae* (Gonococci), *N. meningitidis* (Meningococci), *N, catarrhalis* and *N. flava* (N. = Neisseria);

Corynebacteriaceae, such as Corynebacteria (for example *Corynebacterium diphtheriae, C. pyogenes, C. diphtheroides, C. acnes, C. parvum, C. bovis, C. renale, C. ovis* and *C. murisepticum*), Listeria bacteria (for example *Listeria monocytogenes*), Erysipelothrix bacteria (for example *Erysipelothrix insidiosa*) and Kurthia bacteria (for example *Kurthia zopfii*) (C. = Corynebacterium);

Mycobacteriaceae, such as pathogens of mycobacterioses (for example *Mycobacterium tuberculosis, M. bovis, M. avium*, so-called atypical mycobacteria of the Runyon groups I, II, III and IV, and *M. leprae* (M. = Mycobacterium);

Enterobacteriaceae, such as Escherichiae bacteria of the coli group; (Escherichia bacteria (for example *Escherichia coli*), Enterobacter bacteria (for example *E. aerogenes* and *E. cloacae*), Klebsiella bacteria (for example *K. pneumoniae* and *K. ozaenae*), Erwiniae (for example Erwinia spec., Serratia (for example *Serratia marcescens*) (E. = Enterobacter, K. = Klebsiella), Proteae bacteria of the Proteus group: Proteus (for example *Proteus vulgaris, Pr. morganii, Pr. rettgeri* and *Pr. mirabilis*), Providencia (for example Providencia sp. (Pr. = Proteus), Salmonelleae: Salmonella bacteria (for example *Salmonella paratyphi* A and B, *S, typhi, S. enteritidis S. cholerae suis* and *S. typhimurium* (S. = Salmonella), and Shigella bacteria (for example *Shigella dysenteriae, Sh. ambigua, Sh. flexneri, Sh. boydii* and *Sh. sonnei* (Sh. = Shigella));

Pseudomonadaceae, such as Pseudomonas bacteria (for example *Pseudomonas aeruginosa* and *Pseudomonas pseudomallei*) and Aeromonas bacteria (for example *Aeromonas liquefaciens* and *A. hydrophila* (A. = Aeromonas));

Spirillaceae (such as Vibrio bacteria (for example *Vibrio cholerae, V. proteus* and *V. fetus* (V. = Vibrio)), and Spirillum bacteria (for example *Spirillum minus)*;

Parvobacteriaceae or Brucellaceae, such as Pasteurella bacteria (for example *Pasteurella multocida, Past. pestis* (Yersinia), *Past. pseudotuberculosis* and *Past. tularensis* (Past. = Pasteurella)), Brucella baceteria (for example *Brucella abortus, Br. melitensis* and *Br. suis* (Br. = Brucella)), Haemophilus bacteria (for example *Haemophilus influenzae, H. ducreyi, H. suis, H. canis* and *H. aegypitcus* (H. = Haemophilus)), Bordetella bacteria (for example *Bordetella pertussis* and *B. bronchiseptica* (B. = Bordetella)) and Moraxella bacteria (for example *Moraxella lacunata);*

Bacteroidaceae, such as Bacteroides bacteria (for example *Bacteroides fragilis* and *B. serpens* (B. = Bacteroides)), Fusiform bacteria (for example *Fusobacterium fusiforme*), and Sphaerophorus bacteria (for example *Sphaerophorus necrophorus, Sph. necroticus* and *Sph. pyrogenes* (Sph. = Sphaerophorus));

Bacillaceae, such as aerobic spore-forming organisms (for example *Bacillus anthracis (B. subtilis* and *B. cereus*) (B. = Bacillus)) and anaerobic spore-forming organisms — Clostridia (for example *Clostridium perfringens, Cl. septicium, Cl. oedenatiens, Cl. histolyticum, Cl. tetani* and *Cl. botulinum* (Cl. = Clostridium));

Spirochaetaceae, such as Borrelia bacteria (for example *Borrelia recurrentia* and *B. vincentii* (B. = Borrelia)), Treponema bacteria (for example *Treponema pallidum, Tr. pertinue* and *Tr. carateum* (Tr. Treponema)) and Leptospira bacteria (for example *Leptospira interrogans, Leptospiro icterohaemorrhagiaeL. canicola, L. grippotyphosa, L. pomona, L. mitis* and L. bovis (L. = Leptospira)).

The compounds of the present invention may also be used for the treatment of infections of the respiratory passages and of the pharyngeal cavity, otitis, pharyngitis, pneumonia, peritonitis; pyelonephritis, cystitis, endocarditis, systemic infections, bronchitis and arthritis.

The following in vitro and in vivo activity exemplifies the antibacterial activity of the β-lactams of the present invention and is illustrative of their administrability by the oral route.

1. In vitro experiments

The compounds of the invention were diluted with Muller-Hinton nutrient liquor, with addition of 0.1% of glucose, to a content of 100 μg/ml. The nutrient solution contained, in each case, $1 \times 10^5$ to $2 \times 10^5$ bacterial cells per milliliter. The test tubes containing this charge were in each case incubated for 24 hours and the degree of turbidity was then determined. Freedom from turbidity indicates action. At a dosage of 100 μg/ml the following bacterial cultures were free from turbidity: *E. coli* BE; *Salmonella* sp.; *Shigella* sp.; *Proteus*, indolenegative, sp.; *Pasteurella pseudotuberculosis;* Brucella sp.; *Haemophilus influenzae; Bordetella bronchiseptica; Staphylococcus aureus* 133; *Neisseria catarrhalis* sp.; *Diplococcus pneumoniae* sp.; *Streptococcus pyrogenes* W.; Enterococcus sp.; Lactobacillus sp.; *Corynebacterium diphteriae gravis; Corvnebacterium pyogenes* M; *Clostridium botulin um; Clostridium tetani;* Borrelia sp.

2. In vivo experiments

Table 1 which follows shows the action of the compound from Example 1 against a series of bacteria in animal experiments using white mice. The white mice, of strain $CF_1$, were infected intraperitoneally with the particular species of bacteria mentioned.

The dose, which was subcutaneously administered, is expressed as units of active compound per kg. body weight 1 mole = $5.9514 \times 10^8$ units.

Table 1

Determination of $ED_{50}$ in animal experiments with white mice;

| Microbe | Dose |
|---|---|
| *E. coli* C 165 | $1 \times 100,000$ |
| Staphylococcus aureus 133 | $1 \times 5,000$ |
| Klebsiella | $2 \times 75,000$ |
| Pseudomonas aerug. | $4 \times 150,000$ |

Therapy
1 administration: 30 minutes after infection
2 administrations: 30 minutes and 90 minutes after infection
4 administrations: 30 minutes, 2 hours, 4 hours and 6 hours after infection.

The $ED_{50}$ (ie. the dose at which 50% of the infected animals still survive after 24 hours) was determined after 24 hours.

Other compounds according to the present invention exhibit comparable activity.

The pharmaceutical compositions of the present invention contain a major or minor amount, e.g., 0.1 to 99.5%, preferably 0.5 to 95% of active ingredient as above defined in combination with a pharmaceutically acceptable nontoxic inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of adminstration and the nature and gravity of the illness, generally the dosage will be from 5 to 1000, preferably from 10 to 200, mg/kg of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqeuous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms as sterile solutions and suspensions intended for subcutaneous, intramuscular or intravenous injection. These are prepared by suspending or dissolving a measured amount of the compound in a nontoxic liquid vehicle suitable for injection such as an aqeuous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isoproponal and the like. Other excipients such as emulsifiers, preservatives, colorants, perfumes and the like can also be present. Formulations can also be administered as an aersol, utilizing the usual propellants such as the chlorofluorohydrocarbons.

The preferred daily dose is 0.25 to 100 g, preferably 1 to 20 g, of active ingredient.

Individual administrations are preferably from 1 to 250, and especially 5 to 50, mg/kg of body weight.

While the routes of administration include oral, parenteral (i.e., intramuscular, intraperitoneal, and intravenous), rectal and topical, oral and parenteral application are particularly preferred.

The preferred pharmaceutical compositions are therefore those in a form suitable for oral administration such as tablets, capsules, dragees, pills, and those suitable for parenteral administration such as ampoules of injectable solution.

The present invention also includes growth-promoting compositions which comprise a growth promoting amount of a β-lactam according to the present invention in combination with an edible material and methods of promoting growth which comprise feeding to an animal a growth-promoting amount of a β-lactam according to the present invention. In addition, fodder compositions are included within the present invention. These would comprise an anti-bacterially effective amount of a β-lactam according to the present invention in combination with a nutritious material.

The α-aminobenzylpenicillin used in the Examples contained about 14% of water, but it is equally possible to use anhydrous α-aminobenzylpenicillin (see U.S. Pat. No. 3,144,445).

The α-amino-p.-hydroxybenzypencillin used in the Examples contained about 13% of water, but it is equally possible to use anhydrous α-amino-p.-hydroxybenzylpenicillin.

The 6-[2-amino-2-(1,4-cyclohexadien-1-yl)-acetamido]-penicillanic acid used in the Examples was largely anhydrous.

The 7-(α-amino-phenylacetamido)-3-methyl-ceph-3-em-4-carboxylic acid used in the Examples contained about 5% of the water, but it is equally possible to use anhydrous 7-(α-amino-phenylacetamido)-3-methyl-ceph-3-em-4-carboxylic acid.

The 7-(α-amino-phenylacetamido)-3-acetoxymethyl-ceph-3-em-4-carboxylic acid used in the Examples contained 8% of water, but it is equally possible to use anhydrous 7-(α-aminophenylacetamido-3-acetoxymethyl-ceph-3-em-4-carboxylic acid. "Ampicillin" is α-aminobenzylpenicillin, "amoxicillin" denotes α-amino-p.-hydroxy-benzylpenicillin and "epicillin" denotes α-amino-α-(1,4-cyclohexadien-1-yl)-methylpenicillin, all of which have the D=R configuration in the side-chain. "Cephalexin" is 7-(α-amino-phenylacetamido)-3-methyl-ceph-3-em-4-carboxylic acid and "cephalogylcin" denotes 7-(α-amino-phenylacetamido)-3-acetoxymethyl-ceph-3-em-4-carboxylic acid both of which have the D=R-configuration in the side-chain.

The NMR spectra of the compounds of the invention were recorded in CD₃OD solution. The abbreviations in parentheses denote the followng:

| s = singlet | m = multiplet |
| d = doublet | AB = AB system |
| t = triplet | $A_2B_2$ = $A_2B_2$ system |
| q = quartet | |

The IR spectra of the compounds according to the invention were recorded in Nujol suspension.

The β-lactam content of the compounds of the invention was determined from the extinction of the β-lactamcarbonyl band of the IR spectrum.

Explanation of the abbreviations used in the Examples:
Parts by wt. = parts by weight
Parts by vol. = parts by volume
Hrs. = hours
Hr. = hour
Room temperature = approx. 20° C
The yields quoted in % denote yields in % of theory.

The following nonlimitative examples more particularly illustrate the present invention:

EXAMPLE 1

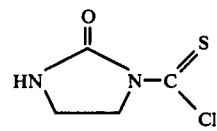

A.

A suspension of 75 parts by wt. of imidazolidin-2-one in 1,500 parts by vol. of tetrahydrofuran is cooled to about 5° C and 69 parts by vol. of thiophosgene are added dropwise while containing to cool with ice, and stirring. The reaction mixture is then stirred overnight at 0° C and thereafter additionally for 3 hrs. at room temperature. The precipitate which is then present is filtered off, combined with the product which after some time crystallises out again from the filitrate, and recrystallised from acetone.

Yield: 53.6 parts by wt. of 1-chlorothiocarbonyl-2-oxo-imidazolidine.

Calculated: C, 29.2; H, 3.0; N, 17.0; S, 19.5%. Found: C, 29.8; H, 3.2; N, 17.0; S, 19.2%.

IR bands in the carbonyl range 1,750 cm⁻¹ (in Nujol)
NMR signals at τ = 5.8–6.7 (m, 4H) (in DMSO-d₆).

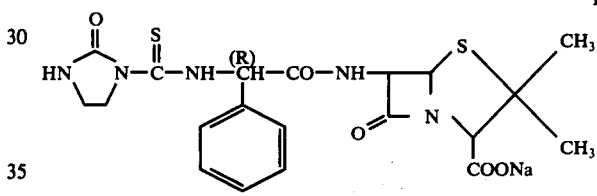

B.

4.0 parts by wt. of ampicillin are dissolved in a mixture of 100 parts by vol. of dichloromethane and 4.2 parts by vol. of triethylene at room temperature. After adding 7.0 parts by wt. of anhydrous magnesium sulphate, the mixture is stirred vigorously for 1 hr. and the drying agent is filtered off. 1.8 parts by wt. of 1-chlorothiocarbonyl-2-oxo-imidazolidine are then added to the filtrate and the mixture is stirred for 3.5 hrs. at room temperature.

The reaction mixture is extracted by stirring with water at pH 7.0 and the aqeuous phase is separated off, covered with a mixture of ether and ethyl acetate (1:1) and acidified, while stirring, until the pH is 2.0. The organic phase is separated off, washed with water and dried over magnesium sulphate and the sodium salt of the penicillin is precipitated with a 1 M sodium 2-ethylhexanoate solution in ether containing methanol. The precipitate is oily. The sodium salt can be converted into a pulverulent form, which can be filtered off, by dissolving it in methanol and precipitating with ether. The salt is filtered off, washed with ether and dried for 2 days over P₄O₁₀ and paraffin chips in a desiccator.

Yield: 3.2 parts by wt. of sodium D-α-[(2-oxo-imidazolidin-1-yl)-thiocarbonylamino]-benzylpenicillin.

β-Lactam content: about 95%.

IR bands in the carbonyl range 1,770, 1,670, 1,610 and 1,535 cm⁻¹ (in Nujol).

NMR signals at = 2.4–2.75 (m, 5H); 4.4 (s, 1H); 4.45–4.65 (AB, 2H); 5.8 (s, 1H); 5.8–6.55 (A₂B₂, 4H) and 8.3–8.6 ppm (d, 6H).

Taking 3% H₂O content into account): Calculated: C, 46.4; H, 4.1; N, 13.6; S, 12.4%. Found: C, 46.2; H, 5.0; N, 13.5; S, 12.5%.

C.

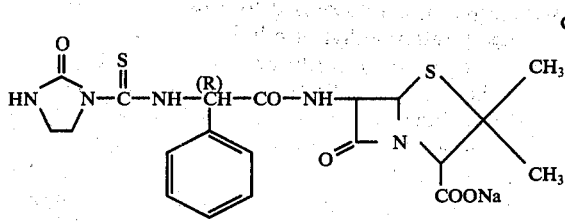

4.0 parts by wt. of ampicillin are dissolved in 40 parts by vol. of 80% strength aqueous tetrahydrofuran at pH 8.0 by adding the amount of triethylamine which just suffices for the purpose.

1.6 parts by wt. of 1-chlorothiocarbonyl-2-oxo-imidazolidine are then introduced at 20° C, while stirring. During this time, and subsequently, the pH of the reaction mixture is kept at 7.0 by suitable addition of triethylamine. The mixture is stirred further until no more triethylamine has to be added to maintain the pH of 7.0 (approx. 1 hr.). The mixture is then diluted with an equal volume of water, the pH is adjusted to 6.5, the tetrahydrofuran is removed in vacuo and the aqeuous solution which remains is covered with a mixture of ether and ethyl acetate (1:1) and acidified to pH 2 while stirring, and cooling gently. The organic phase is then separated off, washed with water and dried over magnesium sulphate, and the sodium salt is then prepared in the manner described under B. (above).

Yield: 3.9 parts by wt. of sodium D-α-[(2-oxo-imidazolidin-1-yl)-thiocarbonylamino]-benzylpenicillin. β-Lactam content: about 91%

IR bands⎫
          ⎬ as for 1B
NMR signals⎭

(Taking 3.8% H₂O content into account): Calculated; C, 46.3; H, 4.6; N, 13.5; S, 12.3%. Found: C, 45.7; H, 5.8; N, 13.1; S, 12.0%.

D.

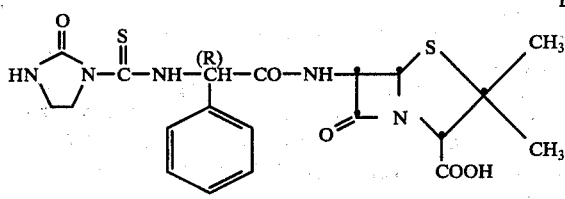

4.0 parts by wt. of ampicillin are dissolved in 40 parts by vol. of water at room temperature and pH 8.0–8.5, with the amount of aqueous 2 N sodium hydroxide solution just required to achieve this. 1.6 parts by wt. of 1-chlorothiocarbonyl-2-oxo-imidazolidine are then introduced over the course of about 15 minutes at 20° C, while stirring. At this same time, and subsequently, the pH is kept at 7.0 by suitable addition of 2 N sodium hydroxide solution. The mixture is stirred for a further 30 minutes at pH 7.0 and is then acidified to pH 2 by means of 1 H HCl while cooling and stirring. The penicillin-acid hereupon precipitates in a crystalline form. It is filtered off after 30 minutes, washed with water and dried in a desiccator.

Yield: 2.8 parts by wt. of D-α-[(2-oxo-imidazolidin-1-yl)-thiocarbonylamino]-benzylpenicillin.

β-Lactam content: about 78%.

IR bands in the carbonyl range 1,790, 1,730, 1700 (shoulder), 1,670 and 1,530 cm⁻¹ (in Nujol).

NMR signals at τ= 2.4–2.8 (m, 5H); 4.5 (s, 1H); 4.35–4.6 (AB, 2H); 5.7 (s, 1H): 5.85–6.6 (A₂B₂, 4H) and 8.35–8.6 ppm (d, 6H).

(Taking 4.8% H₂O content into account): Calculated: C, 47.9; H, 5.1; N, 14.0; S, 12.7%. Found: C, 48.4; H, 4.8; N, 14.0; S, 12.5%.

EXAMPLE 2

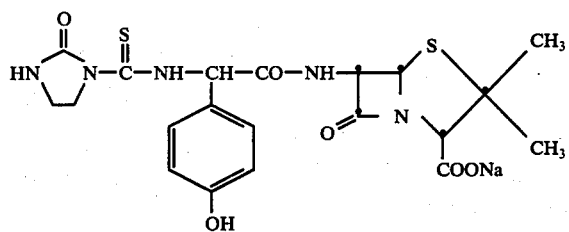

This penicillin sodium salt is prepared analogously to the method described in Example 1 C, from 1.5 parts by wt. of amoxicillin and 0.6 parts by wt. of 1-chlorothiocarbonyl-2-oxo-imidazolidine.

Yield: 1.3 parts by wt. of D-α-[(2-oxo-imidazolidin-1-yl)-thiocarbonylamino]-p-hydroxybenzylpenicillin.

β-Lactam content: about 88%.

IR bands in the carbonyl range 1,770, 1,670, 1,610 and 1,520 cm⁻¹ (in Nujol).

NMR signals at τ= 2.5–3.3 (AB, 4H); 4.25–4.55 (3H); 5.7 (s, 1H); 5.7–6.5 (A₂B₂, 4H) and 8.1–8.5 ppm (d, 6H).

(Taking 8.4% H₂O content into account): Calculated: C, 42.7; H, 4.8; N, 12.4; S, 11.3%. Found: C, 43.4; H, 5.0; N, 11.2; S, 11.0%.

EXAMPLE 3

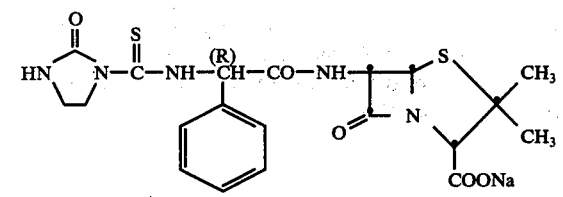

This penicillin sodium salt is prepared analogously to the method described in Example 1 C, from 1.5 parts by wt. of epicillin and 0.8 part by wt. of 1-chlorothiocarbonyl-2-oxo-imidazolidine.

Yield: 1.4 parts by wt. of sodium D -α-[(2-oxo-imidazolidin-1-yl)-thiocarbonylamino]-2,5-dihydro-benzylpenicillin.

β-Lactam content: about 82%.

IR bands in the carbonyl range 1,770, 1,670, 1,610 and 1,530 cm⁻¹ (in Nujol).

NMR signals at τ= 4.05 (s, 1H); 4.3 (s, 2H); 4.5 (s, 2H); 5.05 (s, 1H); 5.8 (s, 1H); 5.8–6.5 (A₂B₂, 4H); 7.25 (s, 4H) and 8.2–8.6 ppm (d, 6H).

EXAMPLE 4

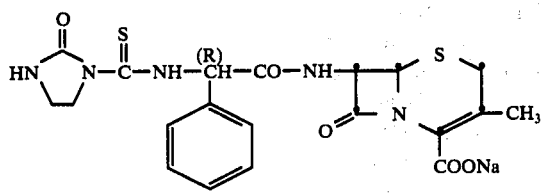

This cephalosporin sodium salt is prepared analogously to the method described in Example 1 C, from 1.0 part by wt. of cephalexin and 0.5 part by wt. of 1-chlorothiocarbonyl-2-oxo-imidazolidine.

Yield: 0.6 part by wt. of sodium 7-{D-α-[2-oxo-imidazolidin-1-yl)-thiocarbonylamino]-phenylacetamido}-3-methyl-ceph-3-em-4-carboxylate.

β-Lactam content: about 85%.

IR bands in the carbonyl range at 1,760, 1,665, (1,590) and 1,530 cm⁻¹ (in Nujol).

(Taking 5.2% H₂O into account): Calculated: C, 45.8; H, 4.4; N, 13.4; S, 12.2%. Found: C, 45.8; H, 4.7; N, 13.3; S, 12.2%.

EXAMPLE 5

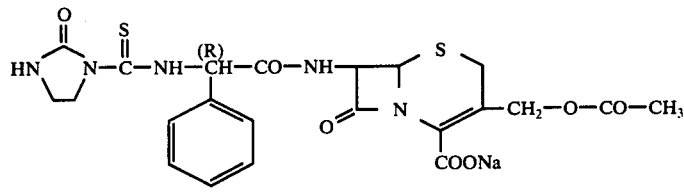

This cephalosporin sodium salt is prepared analogously to the method described in Example 1 C, from 2.2 parts by wt. of cephaloglycine and 0.9 part by wt. of 1-chlorothiocarbonyl-2-oxo-imidazolidine.

Yield: 1.8 parts by wt. of sodium 7-{—α-[(2-oxo-imidazolidin-1-yl)-thiocarbonylamino]-phenylacetamido}-3-acetoxymethyl-ceph-3-em-4-carboxylate.

What is claimed is:

1. A pharmaceutical composition for treating bacterial infections in humans and other animals comprising an antibacterially effective amount of a compound selected from the group consisting of a 2-oxoimidazolidine of the formula:

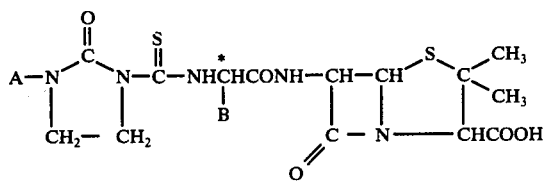

and the pharmaceutically acceptable salts thereof wherein
   the carbon atom designated C* constitutes a center of chirality;
   A is hydrogen or alkyl of 1 to 4 carbon atoms; and
   B is phenyl, methylphenyl, chlorophenyl, hydroxyphenyl or cyclohexa-1,4-dien-1-yl
in combination with a pharmaceutically acceptable nontoxic carrier.

2. A composition according to claim 1 wherein B is phenyl, 4-methylphenyl, 4-chlorophenyl, 4-hydroxyphenyl, or cyclohexa-1,4-dien-1-yl.

3. A composition according to claim 2, wherein A is hydrogen, methyl or ethyl

4. A composition according to claim 1 wherein A is hydrogen or methyl; and
   B is phenyl, 4-methylphenyl, 4-chlorophenyl, 4-hydroxyphenyl, or cyclohexa-1,4-dien-1-yl.

5. A composition according to claim 1 wherein said 2-oxoimidazolidine is α-(2-oxoimidazolidin-1-ylthiocarbonylamino)-benzylpenicillin or the sodium salt thereof.

6. A composition according to claim 1 wherein said 2-oxoimidazolidine is α-(2-oxoimidazolidin-1-ylthiocarbonylamino)-4-hydroxybenzylpenicillin or the sodium salt thereof.

7. A composition according to claim 1 wherein said 2-oxoimidazolidine is α-(2-oxoimidazolidin-1-ylthiocarbonylamino)-2,5-dihydrobenzylpenicillin or the sodium salt thereof.

8. The method of combatting bacterial infections in humans and other animals which comprises administering to said human or other animal an antibacterially effective amount of a compound selected from the group consisting of a 2-oxoimidazolidine of the formula:

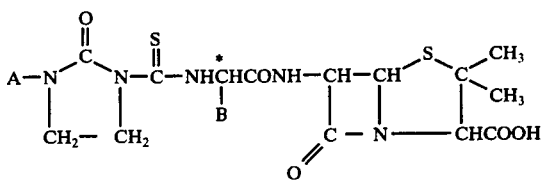

and the pharmaceutically acceptable salts thereof wherein
   the carbon atom designated C* constitutes a center of chirality;
   A is hydrogen or alkyl of 1 to 4 carbon atoms; and
   B is phenyl, methylphenyl, chlorophenyl, hydroxyphenyl or cyclohexa-1,4-dien-1-yl.

9. The method according to claim 8 wherein
   A is hydrogen or methyl; and
   B is phenyl, 4-chlorophenyl, 4-hydroxyphenyl or cyclohexa-1,4-dien-1-yl.

10. The method according to claim 8 wherein said 2-oxoimidazolidine is α-(2-oxoimidazolidin-1-ylthiocarbonylamino)-benzylpenicillin or the sodium salt thereof.

11. The method according to claim 8 wherein said 2-oxoimidazolidine is α-(2-oxoimidazolidin-1-ylthiocarbonylamino)-4-hydroxybenzylpenicillin or the sodium salt thereof.

12. The method according to claim 8 wherein said 2-oxoimidazolidine is α-(2-oxoimidazolidin-1-ylthiocarbonylamino)-2,5-dihydrobenzylpenicillin or the sodium salt thereof.

* * * * *